US009844312B2

(12) United States Patent
Mizuno et al.

(10) Patent No.: US 9,844,312 B2
(45) Date of Patent: Dec. 19, 2017

(54) ENDOSCOPE SYSTEM FOR SUPPRESSING DECREASE OF FRAME RATE WITHOUT CHANGING CLOCK RATE OF READING

(71) Applicant: OLYMPUS CORPORATION, Tokyo (JP)

(72) Inventors: Kyosuke Mizuno, Hino (JP); Saeri Saito, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/245,863

(22) Filed: Aug. 24, 2016

(65) Prior Publication Data

US 2016/0360948 A1     Dec. 15, 2016

Related U.S. Application Data

(63) Continuation of application No. PCT/JP2015/068837, filed on Jun. 30, 2015.

(30) Foreign Application Priority Data

Jul. 7, 2014   (JP) .................................. 2014-139769

(51) Int. Cl.
*A61B 1/045*      (2006.01)
*H04N 5/353*      (2011.01)
(Continued)

(52) U.S. Cl.
CPC ............ *A61B 1/00006* (2013.01); *A61B 1/04* (2013.01); *A61B 1/045* (2013.01); *A61B 1/051* (2013.01);
(Continued)

(58) Field of Classification Search
CPC ....... A61B 1/00006; A61B 1/04; A61B 1/045; A61B 1/0661; H04N 5/2256; H04N 5/235; H04N 5/353; H04N 5/3532; H04N 5/3535

See application file for complete search history.

(56) References Cited

U.S. PATENT DOCUMENTS 8,866,893 B2   10/2014 Ono
9,029,755 B2    5/2015 Ono et al.
(Continued)

FOREIGN PATENT DOCUMENTS

JP     2011135185 A    7/2011
JP     2011250926 A   12/2011
(Continued)

OTHER PUBLICATIONS

Japanese Office Action dated Jan. 26, 2016 issued in corresponding Japanese Patent Application No. JP2015-558277.
(Continued)

*Primary Examiner* — John P Leubecker
(74) *Attorney, Agent, or Firm* — Scully, Scott, Murphy & Presser, P.C.

(57) ABSTRACT

An endoscope system including: a light source that generates illuminating light; a controller that receives a light control signal and controls the illuminating light; a light receiving unit having pixels in a matrix; a reading unit that sequentially reads an electrical signal for each line; and an imaging controller that repeats read processing to sequentially read, for each line, the electrical signal from the light receiving unit, and exposure processing for exposing the light receiving unit. Where a blanking period is a time from completion of reading of a last line for a preceding frame to start of reading of a first line for a following frame and a read period is a time from a start of reading of a first line for a frame to completion of reading of a last line of the frame
(Continued)

such that the blanking period can be changed without changing the read period.

5 Claims, 6 Drawing Sheets

(51) Int. Cl.
    *A61B 1/00*         (2006.01)
    *A61B 1/04*         (2006.01)
    *G03B 15/05*       (2006.01)
    *H04N 5/374*      (2011.01)
    *H04N 9/04*        (2006.01)
    *A61B 1/05*         (2006.01)
    *A61B 1/06*         (2006.01)
    *G02B 23/24*       (2006.01)
    *H04N 5/225*      (2006.01)
    *H04N 5/235*      (2006.01)
    *H04N 9/07*        (2006.01)

(52) U.S. Cl.
    CPC ........ *A61B 1/0676* (2013.01); *G02B 23/2461* (2013.01); *G02B 23/2484* (2013.01); *G03B 15/05* (2013.01); *H04N 5/2256* (2013.01); *H04N 5/2351* (2013.01); *H04N 5/353* (2013.01); *H04N 5/374* (2013.01); *H04N 9/04* (2013.01); *H04N 9/045* (2013.01); *H04N 9/07* (2013.01); *H04N 2005/2255* (2013.01)

(56) References Cited

U.S. PATENT DOCUMENTS

| | | | | |
|---|---|---|---|---|
| 2001/0033333 A1* | 10/2001 | Suzuki | ............. | H01L 27/14609 348/220.1 |
| 2009/0299138 A1* | 12/2009 | Mitsuhashi | ............ | A61B 1/041 600/109 |
| 2013/0201315 A1* | 8/2013 | Takei | ..................... | A61B 1/043 348/77 |
| 2014/0078277 A1* | 3/2014 | Dai | .................... | A61B 1/00004 348/68 |
| 2014/0160260 A1* | 6/2014 | Blanquart | .......... | H04N 5/35554 348/68 |
| 2014/0171737 A1* | 6/2014 | Kagaya | .................. | A61B 1/051 600/109 |
| 2014/0171738 A1* | 6/2014 | Kagaya | .................. | A61B 1/051 600/109 |
| 2014/0198249 A1* | 7/2014 | Tanaka | ................. | H04N 5/2354 348/370 |
| 2015/0116561 A1* | 4/2015 | Takei | ...................... | A61B 1/00 348/296 |
| 2016/0353972 A1* | 12/2016 | Yano | ..................... | A61B 1/045 |

FOREIGN PATENT DOCUMENTS

| | | |
|---|---|---|
| JP | 5427316 B2 | 2/2014 |
| WO | 2013175908 A1 | 11/2013 |

OTHER PUBLICATIONS

Japanese Office Action dated Apr. 26, 2016 issued in corresponding Japanese Patent Application No. JP2015-558277.
International Search Report dated Sep. 29, 2015 issued in corresponding Japanese Patent Application No. PCT/JP2015/068837.

* cited by examiner

ENDOSCOPE SYSTEM FOR SUPPRESSING DECREASE OF FRAME RATE WITHOUT CHANGING CLOCK RATE OF READING

CROSS REFERENCES TO RELATED APPLICATIONS

This application is a continuation of PCT international application Ser. No. PCT/JP2015/068837, filed on Jun. 30, 2015 which designates the United States, incorporated herein by reference, and which claims the benefit of priority from Japanese Patent Application No. 2014-139769, filed on Jul. 7, 2014, incorporated herein by reference.

BACKGROUND

1. Technical Field

The disclosure relates to an endoscope system.

2. Related Art

Conventionally, in the medical field, an endoscope system has been used when observing an organ of a subject such as a patient. The endoscope system includes an endoscope and a processing device, for example. The endoscope includes an insertion portion. The insertion portion has an image sensor at a distal end thereof, has a flexible elongated shape, and is configured to be inserted into a subject. The processing device is connected to a proximal end of the insertion portion through a cable, performs image processing on an in-vivo image according to an imaging signal generated by the image sensor, and causes a display unit to display the in-vivo image.

As an observation method used for the endoscope system, there are a simultaneous lighting and a sequential lighting. In the simultaneous lighting, for example, a color filter that transmits light of three color components of red, green, and blue is provided in front of a light receiving unit of the image sensor and imaging is performed under illuminating light of white light. On the other hand, in the sequential lighting, for example, illuminating light of each of three color components of red, green, and blue is sequentially switched. In the sequential lighting, imaging is performed for each color under illuminating light whose color component is sequentially switched. The sequential lighting has an advantage to be able to reduce the diameter of the insertion portion while maintaining a high image quality as compared with the simultaneous lighting.

As the image sensor, a CMOS (Complementary Metal Oxide Semiconductor) image sensor is used. The CMOS image sensor generates an imaging signal by a rolling shutter method that performs reading by shifting timing for each horizontal line. In the CMOS image sensor, it is possible to arbitrarily set how to read pixel information based on a charge accumulated in a pixel, so that it is possible to perform imaging more variously than a CCD image sensor that reads all the pixels at the same time.

In an endoscope system using a CMOS image sensor, when switching a plurality of types of illumination described above according to a frame rate of an image to be captured, an exposure period may overlap with illumination periods different from each other. In this case, there is a problem that an image in which illuminating rays of light of two different illumination periods are mixed is obtained. As a technique to solve the problem, a technique is disclosed which emits illuminating light of the same color component in a period for at least two frames and excludes an imaging signal of a first frame of imaging signals of a plurality of frames, which are exposed by the illuminating light and read out, from a processing target (for example, see JP 5427316 B1). According to JP 5427316 B1, even when a CMOS image sensor is used, under a condition in which a plurality of illuminating rays of light are switched, it is possible to capture an image corresponding to each illuminating light while securing sufficient sensitivity.

SUMMARY

In some embodiments, an endoscope system includes: a light source unit configured to generate illuminating light to be emitted from a distal end of an insertion portion to be inserted into a subject; an illumination controller configured to receive a light control signal and to control emission of the illuminating light from the distal end of the insertion portion according to the light control signal; a light receiving unit in which a plurality of pixels is provided in a matrix form, each of the plurality of pixels being configured to perform photoelectric conversion on light from the subject irradiated with the illuminating light to generate an electrical signal; a reading unit configured to sequentially read, for each line, the electrical signal generated by each of the pixels; a light control unit configured to generate a first light control signal or a second light control signal, the first light control signal being input to the illumination controller to emit the illuminating light from the distal end of the insertion portion as a first pulsed light in a predetermined illumination period, the second light control signal being input to the illumination controller to emit the illuminating light from the distal end of the insertion portion as a second pulsed light in an illumination period shorter than the predetermined illumination period; and an imaging controller configured to: perform imaging control that alternately repeats read processing for causing the reading unit to sequentially read, for each line, the electrical signal from the light receiving unit, and exposure processing for exposing the light receiving unit; perform imaging control such that, when the first light control signal is generated by the light control unit, the first pulsed light is emitted during a blanking period in which the plurality of pixels is exposed simultaneously; and perform imaging control such that, when the second light control signal is generated by the light control unit, the blanking period is shortened compared to a case where the first light control signal is generated, without changing, from the case where the first light control signal is generated, a read period required for causing the reading unit to read from a first line to a last line in the light receiving unit, and the second pulsed light is emitted during the blanking period.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter referred to as "embodiment(s)") will be described. In the description, as an example of a system including an imaging device according to the present invention, a medical endoscope system that captures and displays an image in a subject such as a patient the image will be described. The present invention is not limited by the embodiments. The same reference signs are used to designate the same elements throughout the drawings.

Embodiments

Figure 1:
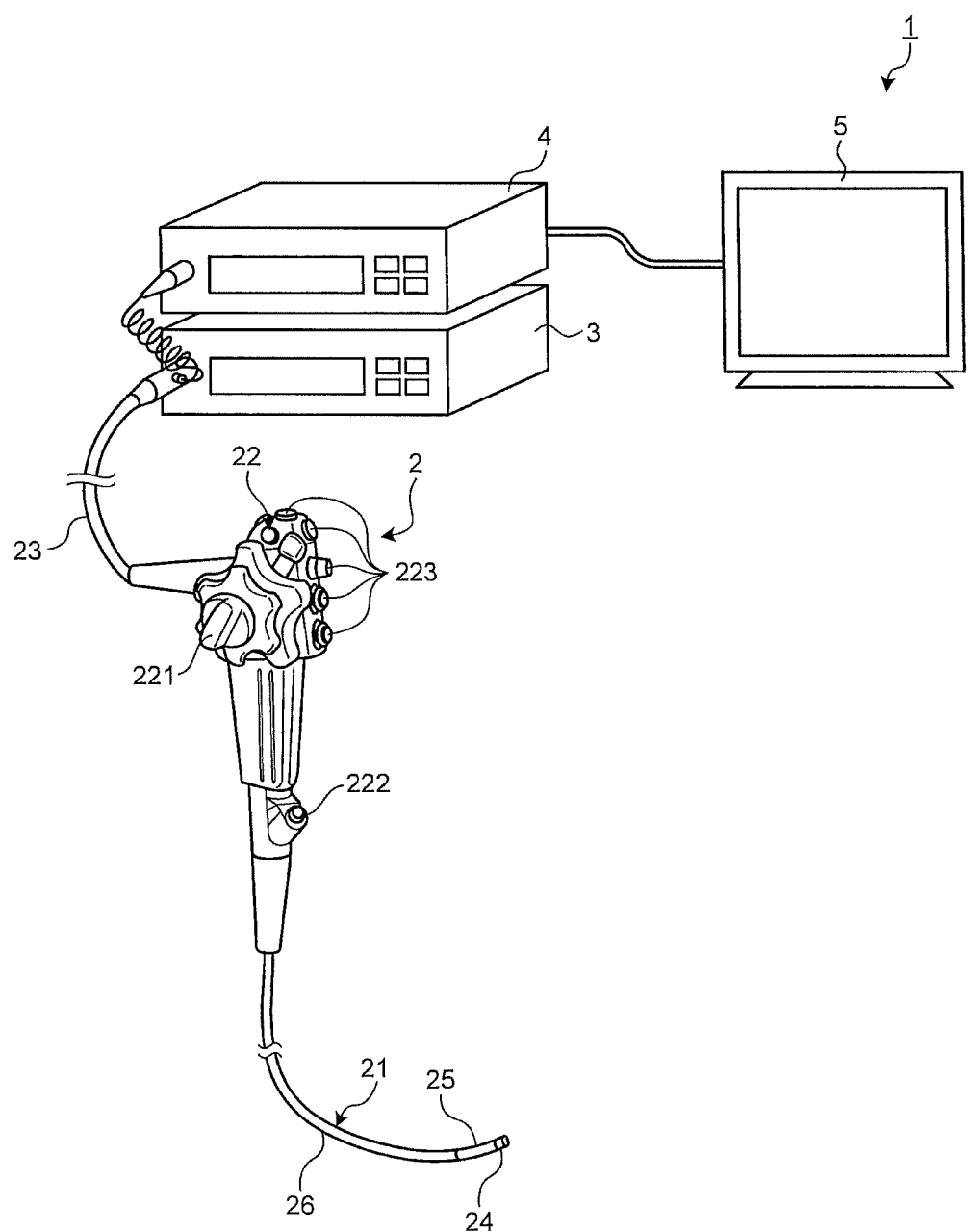
FIG. 1 is a schematic diagram illustrating a configuration of an endoscope system according to an embodiment of the present invention.
Figure 2:
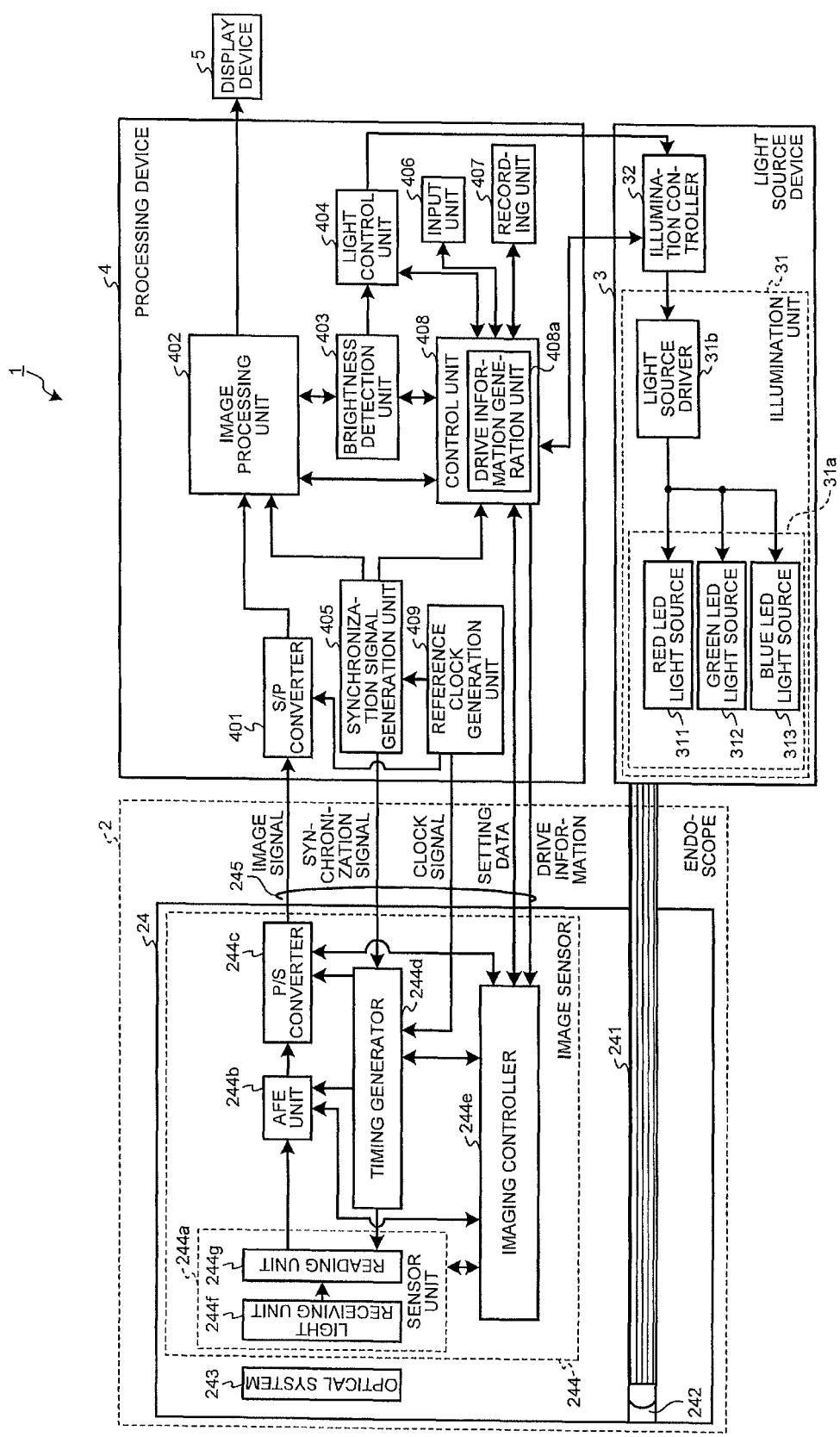
FIG. 2 is a block diagram illustrating a schematic configuration of an endoscope system according to the embodiment of the present invention.

FIG. 1 is a schematic diagram illustrating a configuration of the endoscope system according to the embodiment of the present invention. FIG. 2 is a block diagram illustrating a schematic configuration of the endoscope system according to the embodiment.

An endoscope system 1 illustrated in FIGS. 1 and 2 includes an endoscope 2 that captures an in-vivo image of a subject by inserting its distal end portion into the subject, a light source device 3 that generates illuminating light emitted from the distal end of the endoscope 2, a processing device 4 that performs predetermined image processing on the in-vivo image captured by the endoscope 2 and comprehensively controls an operation of the entire endoscope system 1, and a display device 5 that displays the in-vivo image on which the processing device 4 performs image processing.

The endoscope 2 includes an insertion portion 21 having an elongated shape with flexibility, an operating unit 22 which is connected to the proximal end of the insertion portion 21 and receives inputs of various operation signals, and a universal cord 23 which extends in a direction different from a direction in which the insertion portion 21 extends from the operating unit 22 and includes various cables connected to the light source device 3 and the processing device 4.

The insertion portion 21 includes a distal end portion 24 having an image sensor 244 in which pixels that generate signals by receiving light and performing photoelectric conversion are two-dimensionally arranged, a bendable bending portion 25 configured by a plurality of bending pieces, and an elongated flexible tube portion 26 which has flexibility and is connected to the proximal end of the bending portion 25.

The distal end portion 24 includes a light guide 241 that is configured by using glass fiber and the like and forms a light guide path of the light emitted by the light source device 3, an illumination lens 242 provided at the distal end of the light guide 241, an optical system 243 for collecting light, and the image sensor 244 which is provided at an image forming position of the optical system 243, receives light collected by the optical system 243, photoelectrically converts the light into an electrical signal, and performs predetermined signal processing on the electrical signal.

The optical system 243 is configured by using one or a plurality of lenses and has an optical zoom function that changes an angle of view and a focus function that changes a focal point.

The image sensor 244 includes a sensor unit 244a that generates an electrical signal (imaging signal) by photoelectrically converting light from the optical system 243, an analog front end unit 244b (hereinafter referred to as an "AFE unit 244b") that performs noise elimination and A/D conversion on the imaging signal output from the sensor unit 244a, a P/S converter 244c that performs parallel-serial conversion on the imaging signal (digital signal) output from the AFE unit 244b and transmits the converted imaging signal to the outside, a timing generator 244d that generates pulses for drive timing of the sensor unit 244a and various signal processing in the AFE unit 244b and the P/S converter 244c, and an imaging controller 244e that controls operation of the image sensor 244. The image sensor 244 is realized by using, for example, a monochrome CMOS (Complementary Metal Oxide Semiconductor) image sensor.

The sensor unit 244a includes a light receiving unit 244f in which a plurality of pixels, each of which includes a photodiode that accumulates electric charge according to the amount of light and a capacitor that converts electric charge transferred from the photodiode into a voltage level, are arranged in a matrix form and each pixel photoelectrically converts light from the optical system 243 and generates an electrical signal, and a reading unit 244g that sequentially reads the electrical signal generated by a pixel that is arbitrarily set as a reading target among the plurality of pixels of the light receiving unit 244f and outputs the electrical signal as the imaging signal. The reading unit 244g sequentially reads the electrical signals generated by the plurality of pixels arranged in a matrix form for each horizontal line.

As described above, the image sensor 244 (CMOS image sensor) reads the electrical signal by the rolling shutter method that performs reading by shifting timing for each horizontal line.

The AFE unit 244b includes a noise reduction circuit that reduces noise component included in the analog imaging signal by using, for example, a correlated double sampling (CDS) method, an AGC (Automatic Gain Control) circuit that adjusts an amplification rate (gain) of the electrical signal and maintains a constant output level, and an A/D conversion circuit that A/D converts the imaging signal output as image information through the AGC circuit.

The imaging controller 244e controls various operations of the distal end portion 24 according to setting data received from the processing device 4. For example, the imaging controller 244e outputs a read-out signal to the reading unit 244g and controls an output mode of the electrical signal output from each pixel in units of pixels. The imaging controller 244e is configured by using a CPU (Central Processing Unit), registers that record various programs, and the like.

The operating unit 22 includes a bending knob 221 that bends the bending portion 25 in a vertical direction and a horizontal direction, a treatment tool insertion unit 222 through which treatment tools such as biopsy forceps, an electric scalpel, and an inspection probe are inserted into the subject, and a plurality of switches 223 which is an operation input unit from which an operation instruction signal for peripheral apparatuses such as an air supply means, a water supply means, and a screen display control in addition to the processing device 4 and the light source device 3 is input. The treatment tool inserted from the treatment tool insertion unit 222 is exposed from an opening portion (not illustrated in the drawings) through a treatment tool channel (not illustrated in the drawings) of the distal end portion 24.

The universal cord 23 includes at least the light guide 241 and a cable assembly 245 in which one or more cables are assembled. The cable assembly 245 includes a signal line for transmitting and receiving setting data, a signal line for transmitting and receiving an image signal, a signal line for transmitting and receiving a drive timing signal for driving the image sensor 244, and a signal line for transmitting drive information related to a timing at which the reading unit 244g starts reading.

Next, a configuration of the light source device will be described. The light source device 3 includes an illumination unit 31 and an illumination controller 32.

The illumination unit 31 emits a plurality of illuminating rays of light respectively having different wavelength bands to the object (subject) by sequentially switching the plurality of illuminating rays of light under control of the illumination controller 32. The illumination unit 31 includes a light source unit 31a and a light source driver 31b.

The light source unit 31a includes a red LED light source 311, a green LED light source 312, and a blue LED light source 313, and one or a plurality of lenses. Each LED light source emits light (illuminating light) of its wavelength band under control of the light source driver 31b. The illuminating light generated from the light source unit 31a is emitted from the distal end of the distal end portion 24 to the object through the light guide 241. Specifically, the light source unit 31a emits light having one of wavelength bands of red light (R), green light (G), and blue light (B) (for example, red: 600 nm to 700 nm, green: 500 nm to 600 nm, and blue: 400 nm to 500 nm) as the illuminating light by emitting light from one of the red LED light source 311, the green LED light source 312, and the blue LED light source 313. Thereby, the illumination unit 31 can sequentially emit any one of red light (R illumination), green light (G illumination), and blue light (B illumination) to the endoscope 2 by the light source unit 31a (sequential lighting method).

The light source driver 31b causes the light source unit 31a to emit illuminating light by supplying an electric current to one of the red LED light source 311, the green LED light source 312, and the blue LED light source 313 of the light source unit 31a under control of the illumination controller 32.

The illumination controller 32 controls a type (wavelength band) of illuminating light emitted from the illumination unit 31 by controlling the light source driver 31b to cause the red LED light source 311, the green LED light source 312, and the blue LED light source 313 of the light source unit 31a to turn ON and OFF. The illumination controller 32 receives a synchronization signal from a control unit 408 of the processing device 4, receives a light control signal from a light control unit 404, controls the amount of electric power which the light source driver 31b supplies to the light source unit 31a (each LED light source) based on these signals, and controls a drive timing (a light emitting period) at which the light source driver 31b drives the light source unit 31a. In the light emitting period, the illuminating light may be turned on at all times or the illuminating light may be emitted by pulse driving under the control of the illumination controller 32 by performing PWM (Pulse Width Modulation) control.

Next, a configuration of the processing device 4 will be described. The processing device 4 includes an S/P converter 401, an image processing unit 402, a brightness detection unit 403, the light control unit 404, a synchronization signal generation unit 405, an input unit 406, a recording unit 407, the control unit 408, and a reference clock generation unit 409.

The S/P converter 401 performs serial-parallel conversion on image information (electrical signal) input from the image sensor 244 and outputs the converted image information (electrical signal) to the image processing unit 402.

The image processing unit 402 generates an in-vivo image to be displayed by the display device 5 based on the image information input from the S/P converter 401. The image processing unit 402 generates in-vivo image information including the in-vivo image by performing predetermined image processing on the image information. Here, the image processing includes synchronization processing, optical black subtraction processing, white balance adjustment processing, color matrix calculating processing, gamma correction processing, color reproduction processing, edge enhancement processing, synthesizing processing that synthesizes a plurality of image data, format conversion processing, and the like. The image processing unit 402 outputs the image information input from the S/P converter 401 to the brightness detection unit 403.

The brightness detection unit 403 detects a brightness level corresponding to each pixel from the in-vivo image information input from the image processing unit 402, records the detected brightness level into a memory provided inside the brightness detection unit 403, and outputs the detected brightness level to the control unit 408. Further, the brightness detection unit 403 calculates a gain adjustment value based on the detected brightness level and outputs the gain adjustment value to the image processing unit 402.

The light control unit 404 sets a condition such as the light emitting period (a light emitting start timing and a light emitting end timing) of the light source unit 31a based on a control signal from the control unit 408 and the brightness level detected by the brightness detection unit 403 and outputs the light control signal including the set condition to the light source device 3. Further, the light control unit 404 outputs the set condition to the control unit 408.

The synchronization signal generation unit 405 generates a synchronization signal including at least a vertical synchronization signal based on a clock generated by the reference clock generation unit 409, transmits the synchronization signal to the timing generator 244d through a predetermined signal line included in the cable assembly 245, and transmits the synchronization signal to each unit inside the processing device 4.

The input unit 406 receives inputs of various signals such as an operation instruction signal that instructs an operation of the endoscope system 1.

The recording unit 407 is realized by using a semiconductor memory such as a flash memory and a DRAM (Dynamic Random Access Memory). The recording unit 407 records various programs to cause the endoscope system 1 to operate and data including various parameters necessary for the operation of the endoscope system 1. Further, the recording unit 407 records identification information of the processing device 4. Here, the identification information includes unique information (ID), model year, specification information, transmission method, and transmission rate of the processing device 4.

The control unit 408 is configured by using a CPU and the like. The control unit 408 performs drive control of each element including the image sensor 244 and the light source device 3 and input/output control of information to and from each element. The control unit 408 transmits setting data for imaging control (for example, a pixel to be read) recorded in the recording unit 407 to the imaging controller 244e through a predetermined signal line included in the cable assembly 245.

The control unit 408 includes a drive information generation unit 408a that sets an exposure period in which light from the optical system 243 is exposed to the light receiving unit 244f based on a light emitting period (an illumination period) set by the light control unit 404 and generates drive information including the exposure period. The control unit 408 outputs the drive information generated by the drive information generation unit 408a to the distal end portion 24 and outputs a control signal to cause the illumination unit 31 to perform illumination operation in synchronization with the exposure period to the illumination controller 32. The control signal includes, for example, an illumination start timing and an illumination end timing of the illumination unit 31 according to a read start operation and a read end operation of the reading unit 244g.

The reference clock generation unit 409 generates a clock signal as a reference of operation of each element of the endoscope system 1 and supplies the generated clock signal to each element of the endoscope system 1.

Next, the display device 5 will be described. The display device 5 receives an in-vivo image corresponding to the in-vivo image information generated by the processing device 4 through an image cable and displays the in-vivo image. The display device 5 is configured by using a liquid crystal or an organic EL (Electro Luminescence).

In the embodiments, the imaging device is configured by using the image sensor 244, the illumination unit 31, the illumination controller 32, the light control unit 404, and the drive information generation unit 408a (the control unit 408).

Figure 3:
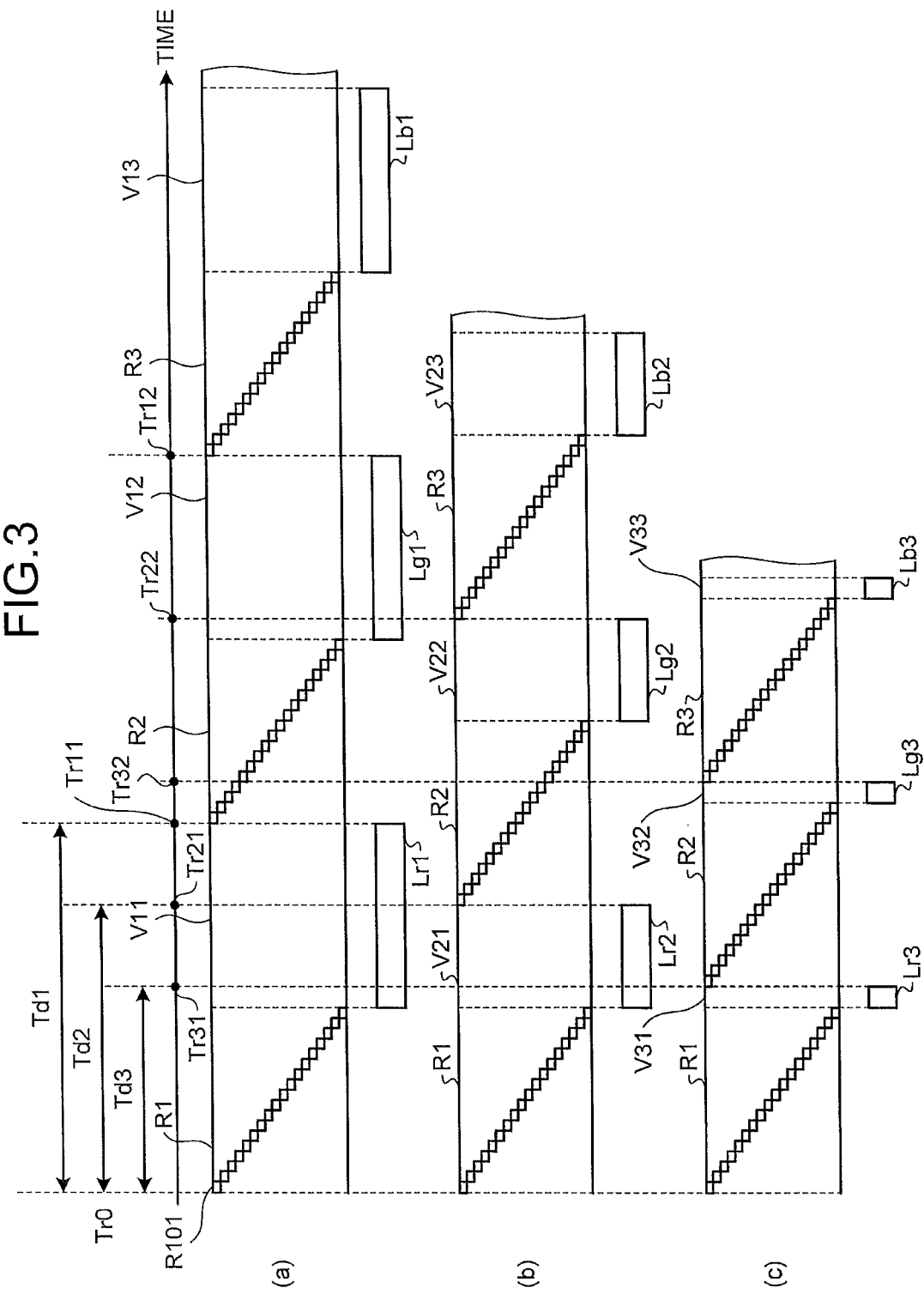
FIG. 3 is an illustrative diagram for explaining a read timing of an image sensor and an illumination timing of an illumination unit of the endoscope system according to the embodiment of the present invention.

Subsequently, a read timing of the image sensor 244 and an illumination timing of the illumination unit 31 of the endoscope system 1 will be described with reference to FIG. 3. FIG. 3 is an illustrative diagram for explaining a read timing of the image sensor and an illumination timing of the illumination unit during imaging of the endoscope system. In FIG. 3, (a) is a diagram when light is emitted during a period in which the amount of light emission is the maximum. In FIG. 3, (b) is a diagram when light is emitted during a period in which the amount of light emission is about a half of the maximum amount of light emission. In FIG. 3, (c) is a diagram when light is emitted during a period in which the amount of light emission is sufficiently smaller than the maximum amount of light emission.

The image sensor 244 acquires an imaging signal including an in-vivo image of the subject by alternately repeating a read period in which the reading unit 244g performs read processing of electrical signals of first to nth lines (one frame) by shifting timing for every horizontal line and a vertical blanking period which is a period different from the read period and is a period (exposure period) in which exposure processing of the light receiving unit 244f (illumination to an area to be imaged by illuminating light) is performed. For example, in (a) of FIG. 3, read periods R1 to R3 and vertical blanking periods V11 to V13 are alternately repeated. In (a) of FIG. 3, for example, the read period of the first line is indicated by a period R101.

First, reference will be made to a case in which illumination is performed by the illumination unit 31 in an illumination period in which the amount of light emission is a set maximum amount (a full light emitting period), with reference to (a) of FIG. 3. When the illumination period is set to be the full light emitting period by the light control unit 404, the drive information generation unit 408a generates drive information in which the vertical blanking period (the exposure period) is set to be the same period as the illumination period.

As illustrated in (a) of FIG. 3, when an operation of the reading unit 244g is reset at the time Tr0 by the imaging controller 244e, the reading unit 244g starts reading of the first to the nth lines (one frame). In the embodiments, the imaging controller 244e outputs a reset signal (a vertical synchronization signal) at a start timing when the reading unit 244g starts reading (a timing when the next frame is started) based on the drive information (the exposure period) generated by the drive information generation unit 408a. Thereby, the imaging controller 244e resets an operation (specifically, a capacitor) according to a timing when the reading unit 244g starts reading and causes the reading unit 244g to start a read operation.

When the read operation of the reading unit 244g ends in the read period R1, the imaging controller 244e proceeds to the vertical blanking period V11. In the vertical blanking period V11, the illumination unit 31 emits illuminating light in synchronization with the vertical blanking period V11 and the illuminating light exposes the light receiving unit 244f. Specifically, when an illumination period Lr1 is set to be the full light emitting period by the light control unit 404, the drive information generation unit 408a generates drive information in which the vertical blanking period V11 (exposure period) is set to be the same period as the illumination period Lr1. In the illumination period Lr1, red light (R illumination) is emitted by control of the illumination controller 32. The R illumination is performed in synchronization with the vertical blanking period V11, so that the light receiving unit 244f is exposed by light (observation light) reflected or scattered from an imaging target by the R illumination in the vertical blanking period V11.

Thereafter, the imaging controller 244e outputs a reset signal to reset the operation at a timing (time Tr11) when the vertical blanking period V11 ends, proceeds to the read period R2, and causes the reading unit 244g to start the read operation. An electrical signal which is read by the reading unit 244g at this time is an electrical signal generated by the red light received by the light receiving unit 244f in the vertical blanking period V11 (the illumination period Lr1).

When the read operation of the reading unit 244g ends in the read period R2, the imaging controller 244e proceeds to the vertical blanking period V12. In the vertical blanking period V12, the illumination unit 31 emits illuminating light in synchronization with the vertical blanking period V12 and the illuminating light exposes the light receiving unit 244f. Specifically, when an illumination period Lg1 is set to be the full light emitting period in the same manner as in the illumination period Lr1, the drive information generation unit 408a generates drive information in which the vertical blanking period V12 is set to be the same period as the illumination period Lg1. In the illumination period Lg1, green light (G illumination) is emitted under the control of the illumination controller 32. The G illumination is performed in synchronization with the vertical blanking period V12, so that the light receiving unit 244f is exposed by observation light of the G illumination in the vertical blanking period V12.

Thereafter, the imaging controller 244e outputs a reset signal to reset the operation at a timing (time Tr12) when the vertical blanking period V12 ends, proceeds to the read period R3, and causes the reading unit 244g to start the read operation. An electrical signal which is read by the reading unit 244g at this time is an electrical signal generated by the green light received by the light receiving unit 244f in the vertical blanking period V12 (the illumination period Lg1).

When the read operation of the reading unit 244g ends in the read period R3, the imaging controller 244e proceeds to the vertical blanking period V13. In the vertical blanking period V13, the illumination unit 31 emits illuminating light in synchronization with the vertical blanking period V13 and the illuminating light exposes the light receiving unit 244f. Specifically, when an illumination period Lb1 is set to be the full light emitting period in the same manner as in the illumination period Lr1, the drive information generation unit 408a generates drive information in which the vertical blanking period V13 is set to be the same period as the illumination period Lb1. In the illumination period Lb1, blue light (B illumination) is emitted under the control of the illumination controller 32. The B illumination is performed in synchronization with the vertical blanking period V13, so that the light receiving unit 244f is exposed by observation light of the B illumination in the vertical blanking period V13.

Thereafter, in the same manner as that of the processing described above, the imaging controller 244e resets the operation at a timing when the vertical blanking period V13 ends, proceeds to the next read period, and causes the reading unit 244g to start the read operation. An electrical signal which is read by the reading unit 244g at this time is an electrical signal generated by the blue light received by the light receiving unit 244f in the vertical blanking period V13 (the illumination period Lb1).

Next, a case in which illumination is performed by the illumination unit 31 in an illumination period (a half light emitting period) in which the amount of light emission is about a half of the maximum amount of light emission will be described with reference to (b) of FIG. 3. When the illumination period is set to be the half light emitting period by the light control unit 404, the drive information generation unit 408a generates drive information in which the vertical blanking period (the exposure period) is set to be the same period as the illumination period.

In the same manner as that of the processing described above, when an operation of the reading unit 244g is reset at the time Tr0 by the imaging controller 244e, the reading unit 244g starts reading for each horizontal line. When the read operation of the reading unit 244g ends in the read period R1, the imaging controller 244e proceeds to the vertical blanking period V21. In the vertical blanking period V21, the illumination unit 31 emits illuminating light in synchronization with the vertical blanking period V21 and the illuminating light exposes the light receiving unit 244f. Specifically, when an illumination period Lr2 is set to be the half light emitting period by the light control unit 404, the drive information generation unit 408a generates drive information in which the vertical blanking period V21 (exposure period) is set to be the same period as the illumination period Lr2. In the illumination period Lr2, R illumination is performed under the control of the illumination controller 32. The R illumination is performed in synchronization with the vertical blanking period V21, so that the light receiving unit 244f is exposed by observation light of the R illumination in the vertical blanking period V21.

Thereafter, the imaging controller 244e resets the operation at a timing (time Tr21) when the vertical blanking period V21 ends, proceeds to the read period R2, and causes the reading unit 244g to start the read operation. An electrical signal which is read by the reading unit 244g at this time is an electrical signal generated by the red light received by the light receiving unit 244f in the vertical blanking period V21 (the illumination period Lr2).

When the read operation of the reading unit 244g ends in the read period R2, the imaging controller 244e proceeds to the vertical blanking period V22. In the vertical blanking period V22, the illumination unit 31 emits illuminating light in synchronization with the vertical blanking period V22 and the illuminating light exposes the light receiving unit 244f. Specifically, when an illumination period Lg2 is set to be the half light emitting period in the same manner as in the illumination period Lr2, the drive information generation unit 408a generates drive information in which the vertical blanking period V22 is set to be the same period as the illumination period Lg2. In the illumination period Lg2, G illumination is performed under the control of the illumination controller 32. The G illumination is performed in synchronization with the vertical blanking period V22, so that the light receiving unit 244f is exposed by observation light of the G illumination in the vertical blanking period V22.

Thereafter, the imaging controller 244e resets the operation at a timing (time Tr22) when the vertical blanking period V22 ends, proceeds to the read period R3, and causes the reading unit 244g to start the read operation. An electrical signal which is read by the reading unit 244g at this time is an electrical signal generated by the green light received by the light receiving unit 244f in the vertical blanking period V22 (the illumination period Lg2).

When the read operation of the reading unit 244g ends in the read period R3, the imaging controller 244e proceeds to the vertical blanking period V23. In the vertical blanking period V23, the illumination unit 31 emits illuminating light in synchronization with the vertical blanking period V23 and the illuminating light exposes the light receiving unit 244f. Specifically, when an illumination period Lb2 is set to be the half light emitting period in the same manner as in the illumination period Lr2, the drive information generation unit 408a generates drive information in which the vertical blanking period V23 is set to the same period as the illumination period Lb2. In the illumination period Lb2, B illumination is performed under the control of the illumination controller 32. The B illumination is performed in synchronization with the vertical blanking period V23, so that the light receiving unit 244f is exposed by observation light of the B illumination in the vertical blanking period V23.

Thereafter, in the same manner as that of the processing described above, the imaging controller 244e resets the operation at a timing when the vertical blanking period V23 ends, proceeds to the next read period, and causes the reading unit 244g to start the read operation. An electrical signal which is read by the reading unit 244g at this time is an electrical signal generated by the blue light received by the light receiving unit 244f in the vertical blanking period V23 (the illumination period Lb2).

Next, a case in which illumination is performed by the illumination unit 31 in an illumination period (a minimum light emitting period) in which the amount of light emission is sufficiently smaller than the maximum amount of light emission that can be emitted will be described with reference to (c) of FIG. 3. When the illumination period is set to be the minimum light emitting period by the light control unit 404, the drive information generation unit 408a generates drive information in which the vertical blanking period (the exposure period) is set to be the same period as the illumination period.

In the same manner as that of the processing described above, when an operation of the reading unit 244g is reset at the time Tr0 by the imaging controller 244e, the reading unit 244g starts reading for each horizontal line. When the read operation of the reading unit 244g ends in the read period R1, the imaging controller 244e proceeds to the vertical blanking period V31. In the vertical blanking period V31, the illumination unit 31 emits illuminating light in synchronization with the vertical blanking period V31 and the illuminating light exposes the light receiving unit 244f. Specifically, when an illumination period Lr3 is set to be the minimum light emitting period by the light control unit 404, the drive information generation unit 408a generates drive information in which the vertical blanking period V31 (exposure period) is set to be the same period as the illumination period Lr3. In the illumination period Lr3, R illumination is performed under the control of the illumination controller 32. The R illumination is performed in synchronization with the vertical blanking period V31, so that the light receiving unit 244f is exposed by observation light of the R illumination in the vertical blanking period V31.

Thereafter, the imaging controller 244e resets the operation at a timing (time Tr31) when the vertical blanking period V31 ends, proceeds to the read period R2, and causes the reading unit 244g to start the read operation. An electrical signal which is read by the reading unit 244g at this time is an electrical signal generated by the red light received by the light receiving unit 244f in the vertical blanking period V31 (the illumination period Lr3).

When the read operation of the reading unit 244g ends in the read period R2, the imaging controller 244e proceeds to the vertical blanking period V32. In the vertical blanking period V32, the illumination unit 31 emits illuminating light in synchronization with the vertical blanking period V32 and the illuminating light exposes the light receiving unit 244f. Specifically, when an illumination period Lg3 is set to be the minimum light emitting period in the same manner as in the illumination period Lr3, the drive information generation unit 408a generates drive information in which the vertical blanking period V32 is set to be the same period as the illumination period Lg3. In the illumination period Lg3, G illumination is performed under the control of the illumination controller 32. The G illumination is performed in synchronization with the vertical blanking period V32, so that the light receiving unit 244f is exposed by observation light of the G illumination in the vertical blanking period V32.

Thereafter, the imaging controller 244e resets the operation at a timing (time Tr32) when the vertical blanking period V32 ends, proceeds to the read period R3, and causes the reading unit 244g to start the read operation. An electrical signal which is read by the reading unit 244g at this time is an electrical signal generated by the green light received by the light receiving unit 244f in the vertical blanking period V32 (the illumination period Lg3).

When the read operation of the reading unit 244g ends in the read period R3, the imaging controller 244e proceeds to the vertical blanking period V33. In the vertical blanking period V33, the illumination unit 31 emits illuminating light in synchronization with the vertical blanking period V33 and the illuminating light exposes the light receiving unit 244f. Specifically, when an illumination period Lb3 is set to be the minimum light emitting period in the same manner as in the illumination period Lr3, the drive information generation unit 408a generates drive information in which the vertical blanking period V33 is set to be the same period as the illumination period Lb3. In the illumination period Lb3, B illumination is performed under the control of the illumination controller 32. The B illumination is performed in synchronization with the vertical blanking period V33, so that the light receiving unit 244f is exposed by observation light of the B illumination in the vertical blanking period V33.

Thereafter, in the same manner as that of the processing described above, the imaging controller 244e resets the operation at a timing when the vertical blanking period V33 ends, proceeds to the next read period, and causes the reading unit 244g to start the read operation. An electrical signal which is read by the reading unit 244g at this time is an electrical signal generated by the blue light received by the light receiving unit 244f in the vertical blanking period V33 (the illumination period Lb3).

As described above, by setting the vertical blanking period according to the illumination period of the illuminating light, it is possible to reduce a time from when a reset operation is performed to when the next reset operation is performed (a time from a read start timing of the mth (m is a natural number) frame to a read start timing of the (m+1)th frame) according to the illumination period. For example, as illustrated in FIG. 3, when a time from the time Tr0 to the time Tr11 is Td1, a time from the time Tr0 to the time Tr21 is Td2, and a time from the time Tr0 to the time Tr31 is Td3, Td3<Td2<Td1 is established. Specifically, for example, when the longest illumination period is 16.68 ms, the illumination period corresponding to about a half of the maximum amount of light emission is 12.68 ms, and the illumination period corresponding to about the minimum amount of light emission is 8.68 ms, it is possible to reduce the frame rate by 8.0 ms at most per frame while the clock rate of the reading is maintained.

The time required for one frame is reduced in this way, so that it is possible to reduce the time required to read a plurality of frames (the time required for acquisition processing of electrical signals of a plurality of frames). Thereby, for example, an acquisition time of each frame exposed by red light, green light, and blue light is reduced and it is possible to reduce color shift generated when synthesizing images of three color components. In general, the smaller (closer) the distance between the imaging target and the distal end portion 24 (the optical system 243), the more sufficiently the light can be applied to the imaging target, so that it is possible to obtain sufficient brightness even if illumination time is reduced. In the embodiments, in particular, the smaller (closer) the distance between the imaging target and the distal end portion 24 (the optical system 243), the more reliably the color shift can be reduced and a clear image can be acquired, so that it is possible to obtain further effects.

On the other hand, in prior arts, although the light control unit controls the amount of light emission and the illumination period, the vertical blanking period is not set according to the illumination period, so that the time during which the reset operation is performed is not changed. Therefore, the vertical blanking period is set to be larger than the maximum period in which light can be emitted or even when the illumination period is reduced, the reduced period becomes a blank period in which neither read processing nor illumination processing is performed.

Further, in the embodiments, only the vertical blanking period is set according to the illumination period and the read period is constant without being reduced according to the illumination period, so that it is not required to set the clock rate of the reading to high speed. Therefore, it is possible to maintain stable read processing.

According to the embodiments described above, the drive information generation unit 408a sets the vertical blanking period (the exposure period) according to the illumination period, for example, when the illumination period is reduced, the drive information generation unit 408a generates drive information in which the vertical blanking period is reduced, the image sensor 244 performs read processing and exposure processing based on the drive information, and the light source device 3 performs illumination processing in synchronization with the exposure processing, so that it is possible to suppress decrease of the frame rate without changing the clock rate of the reading.

Further, according to the embodiments described above, the illumination period is set only in the vertical blanking period and the illumination period does not include the read period, so that the exposure period of each horizontal line becomes the same and it is possible to suppress difference in brightness between horizontal lines.

First Modified Example

Figure 4:
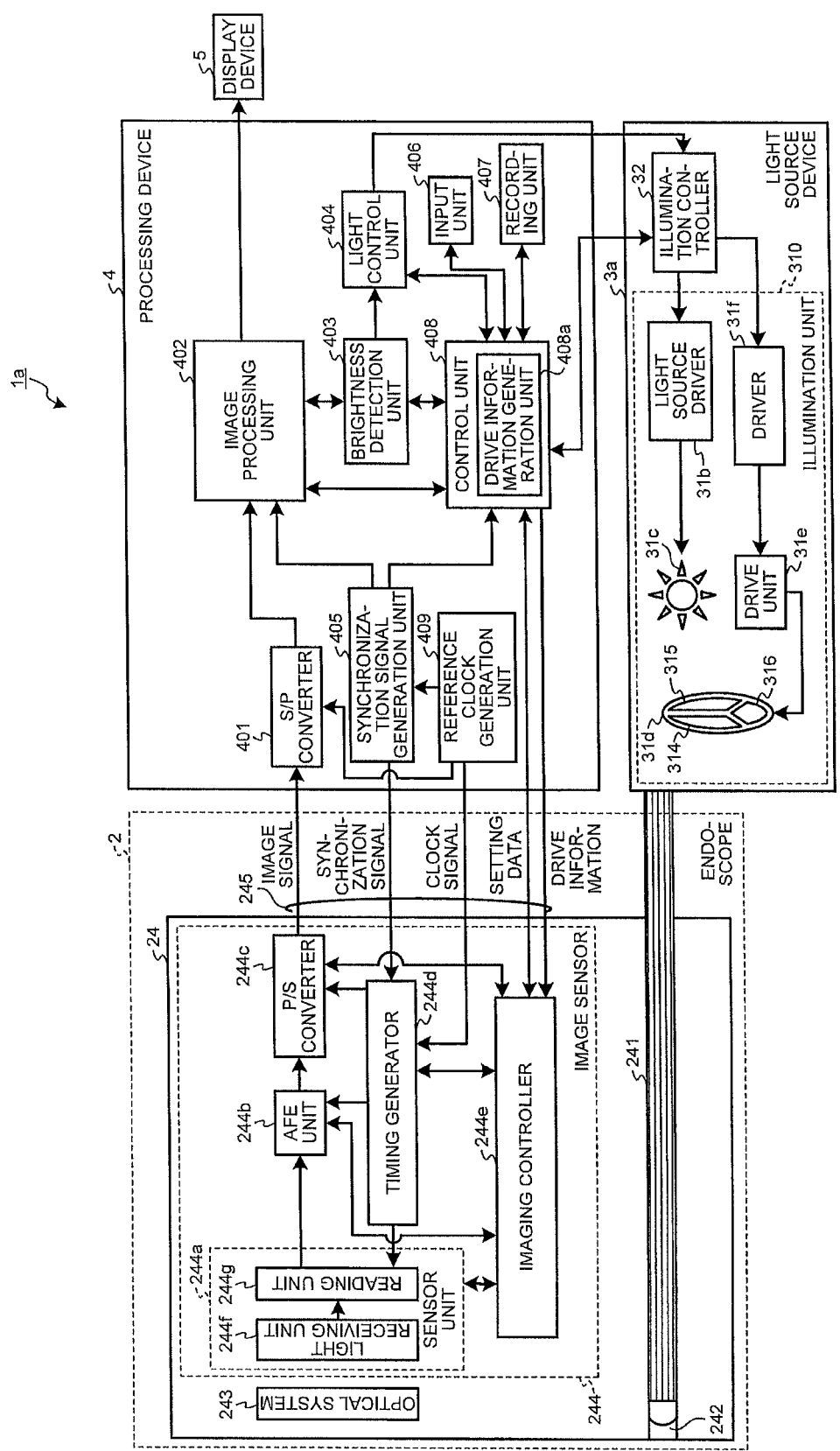
FIG. 4 is a block diagram illustrating a schematic configuration of an endoscope system according to a first modified example of the embodiment of the present invention.

Next, a first modified example of the embodiment of the present invention will be described. FIG. 4 is a block diagram illustrating a schematic configuration of an endoscope system according to the first modified example of the embodiment of the present invention. The same reference signs are used to refer to the same elements as those described above. In the embodiments described above, the light source device 3 has a plurality of light sources that emit rays of light of different wavelength bands. However, an endoscope system 1a according to the first modified example includes one light source and a rotating filter that can transmit a plurality of illuminating rays of light whose wavelength bands are different from each other.

The light source device 3a of the endoscope system 1a according to the first modified example includes an illumination unit 310 and an illumination controller 32. The illumination unit 310 emits a plurality of illuminating rays of light respectively having different wavelength bands to an object (subject) by sequentially switching between the plurality of illuminating rays of light under control of the illumination controller 32. The illumination unit 310 has the light source driver 31b described above, a light source unit 31c, a rotating filter 31d, a drive unit 31e, and a driver 31f.

The light source unit 31c includes a white LED light source and one or a plurality of lenses and emits white light to the rotating filter 31d under control of the light source driver 31b. The white light generated by the light source unit 31c is emitted from the distal end of the distal end portion 24 to the object through the rotating filter 31d and the light guide 241.

The rotating filter 31d is arranged on an optical path of the white light emitted from the light source unit 31c and rotates to cause only light having a predetermined wavelength band among the white light emitted from the light source unit 31c to pass through the rotating filter 31d. Specifically, the rotating filter 31d includes a red color filter 314, a green filter 315, and a blue filter 316 which causes rays of light having wavelength bands of red light (R), green light (G), and blue light (B) to pass through, respectively. The rotating filter 31d rotates to cause rays of light having the wavelength bands of red, green, and blue (for example, red: 600 nm-700 nm, green: 500 nm-600 nm, blue: 400 nm-500 nm) to pass through sequentially. Thereby, the illumination unit 310 can sequentially emit any one of narrow-banded red light (R illumination), green light (G illumination), and blue light (B illumination) among the white light (W illumination) emitted from the light source unit 31c to the endoscope 2 (sequential lighting method).

The drive unit 31e is configured by using a stepping motor, a DC motor, or the like, and rotates the rotating filter 31d. It is possible to change transmission interval of rays of light of wavelength bands of red, green, and blue by changing a rotating speed of the drive unit 31e.

The driver 31f supplies a predetermined electric current to the drive unit 31e under control of the illumination controller 32.

In the first modified example, the illumination controller 32 controls the light source driver 31b to turn on the white LED light source of the light source unit 31c and controls a type (wavelength band) and a light emitting period of the illuminating light emitted from the illumination unit 310 by controlling the driver 31f to rotate the rotating filter 31d at a specified speed. The illumination controller 32 receives a synchronization signal from the control unit 408 of the processing device 4, receives a light control signal from the light control unit 404, and controls the amount of electric power which the light source driver 31b supplies to the light source unit 31c based on these signals. The light source driver 31b may turns on the illuminating light at all times while the illuminating light is blocked by the rotating filter 31d during the vertical blanking period, may control a drive timing (light emitting period) for driving the light source unit 31c in accordance with the vertical blanking period, and may PWM-control the drive timing (light emitting period) for driving the light source unit 31c during the light emitting period so that the illumination unit 310 emits pulse-driven illuminating light under the control of the illumination controller 32.

Second Modified Example

Figure 5:
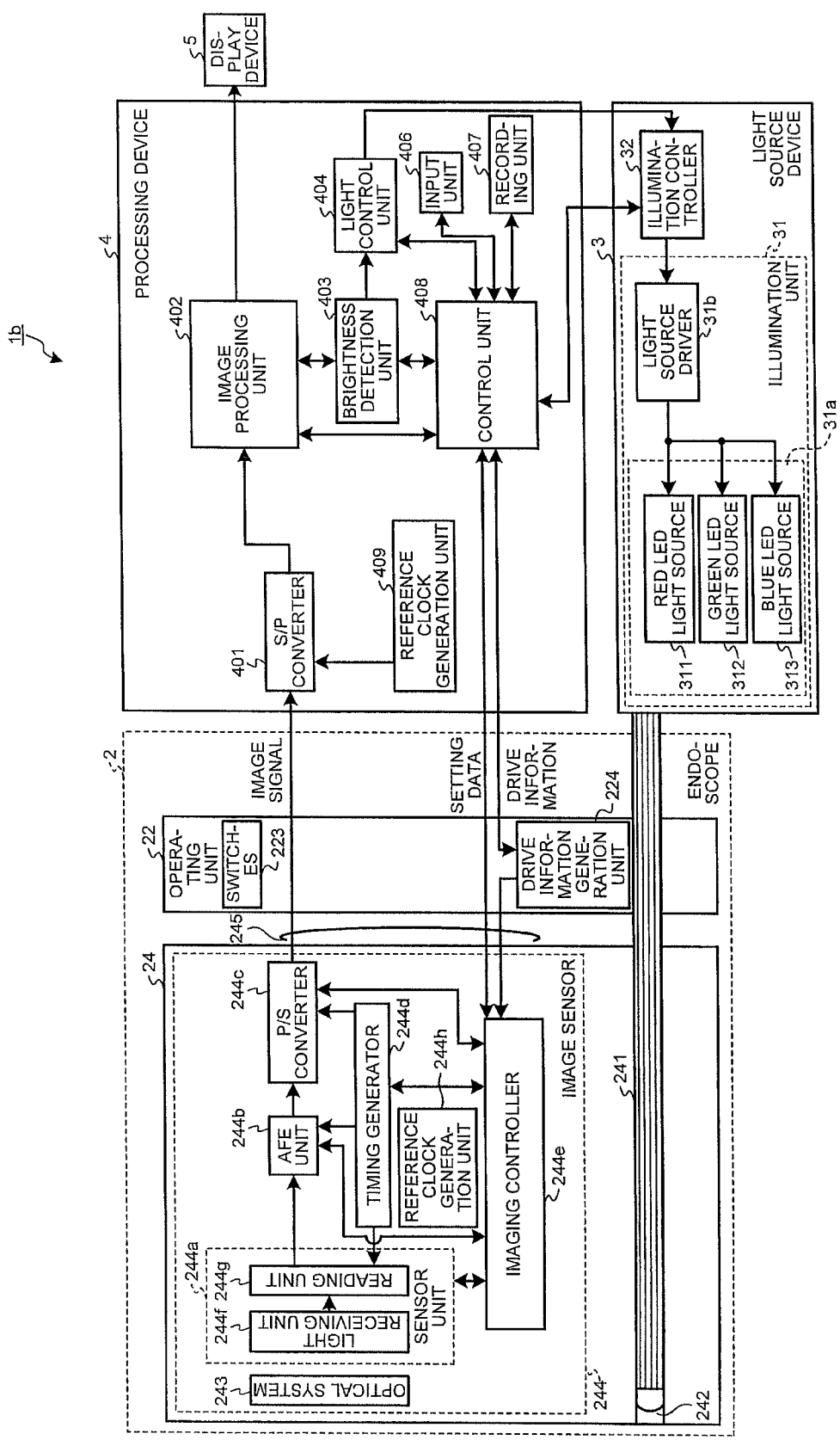
FIG. 5 is a block diagram illustrating a schematic configuration of an endoscope system according to a second modified example of the embodiment of the present invention.

Next, a second modified example of the embodiment of the present invention will be described. FIG. 5 is a block diagram illustrating a schematic configuration of an endoscope system according to the second modified example of the embodiment of the present invention. The same reference signs are used to refer to the same elements as those described above. In the embodiments described above, the drive information generation unit 408a provided in the processing device 4 controls the read timing and the illumination timing. However, in the second modified example, a drive information generation unit 224 is provided in the endoscope 2 (the operating unit 22) and the read timing and the illumination timing are controlled based on a control signal generated by the drive information generation unit 224.

In an endoscope system 1b according to the second modified example, the image sensor 244 of the endoscope 2 described above further includes a reference clock generation unit 244h. In the second modified example, the reference clock generation unit 244h is provided in the image sensor 244, and the read start timing and irradiation timing of the illuminating light are controlled by a clock generated by the reference clock generation unit 244h. In other words, in the endoscope system 1b, the reading timing by the reading unit 244g and the illumination timing by the illumination controller 32 are controlled by using the clock generated by the reference clock generation unit 244h as a reference. In the second modified example, the light source device 3 operates based on the clock generated by the reference clock generation unit 244h, and the reference clock generation unit 409 generates a clock for operating elements in the processing device 4, such as the image processing unit 402. The endoscope system 1b does not have the drive information generation unit 408a described above. In the second modified example, the imaging device is formed by using the image sensor 244, the illumination unit 31, the illumination controller 32, the light control unit 404, and the drive information generation unit 224.

The operating unit 22 according to the second modified example includes the drive information generation unit 224 that acquires the illumination period set by the light control unit 404 from the processing device 4 and generates drive information related to the vertical blanking period (the exposure period) according to the illumination period and the illumination timing of the illumination unit 31. The drive information generation unit 224 outputs the generated drive information to the distal end portion 24 and the processing device 4. The drive information according to the modified example is information including the read start timing of each frame (the vertical synchronization signal) and the illumination start timing and the illumination end timing of the illumination unit 31. The clock generated by the reference clock generation unit 244h may be superimposed on the drive information or the reference clock or a clock synchronized with the reference clock (not illustrated in the drawings) may be received from the processing device 4.

When the control unit 408 receives the drive information from the drive information generation unit 224, the control unit 408 outputs a control signal related to the illumination start timing and the illumination end timing to the illumination controller 32. In the same manner as in the embodiment described above, the illumination controller 32 performs illumination control by controlling the illumination unit 31 in synchronization with the vertical blanking period. The illumination controller 32 performs control of the illumination unit 31 based on the clock generated by the reference clock generation unit 244h.

According to the second modified example, it is possible to perform illumination control by synchronizing the vertical blanking period with the illumination period based on a clock generated in the endoscope 2. The setting of the vertical blanking period according to the illumination period by the drive information generation unit 224 is the same as the setting processing of the drive information generation unit 408a according to the embodiment described above.

Here, in the embodiments described above, the light control unit 404 sets the illumination period according to a detection result of the brightness detection unit 403 and the vertical blanking period is set according to the illumination period set by the drive information generation unit 408a. However, in the second modified example, the drive information generation unit 224 may acquire the illumination period set by the light control unit 404 and set the vertical blanking period or may acquire luminance information from the AFE unit 244b or the like, set the illumination period and the vertical blanking period, and output the set illumination period (including an illumination timing and the like) to the control unit 408 as the drive information.

In the second modified example, the operating unit 22 includes the drive information generation unit 224. However, a drive information generation unit may be provided in the image sensor 244, for example, in the imaging controller 244e, and drive information generated by the drive information generation unit may be output to the processing device 4. Further, as in the first modified example described above, the wavelength band of the illuminating light may be selected by the rotating filter 31d.

In the embodiments, it is preferable that the read start timing of the first line is a first horizontal line of lines including an effective pixel area to acquire an image of the effective pixel area.

In the embodiments, the vertical blanking period is set according to the illumination period. However, for example, when there is a pixel not to be read or a pixel (horizontal line) not to be image-processed in the read period R1, a period required to read the pixel not to be read may be included in the vertical blanking period (the exposure period). In other words, when pixels other than pixels to be read and pixels to be image-processed are set, a period required to read the set pixels may be assumed to be a part of the vertical blanking period.

Figure 6:
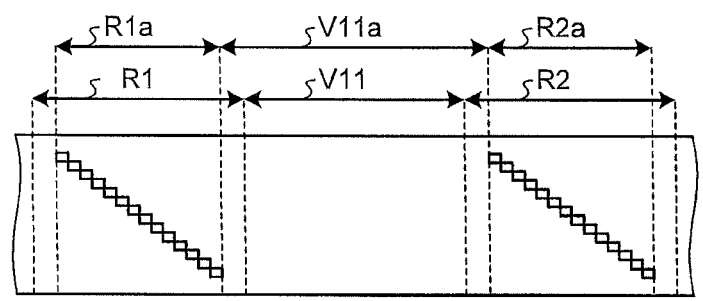
FIG. 6 is an illustrative diagram for explaining a read timing of an image sensor and an illumination timing of an illumination unit of the endoscope system according to the embodiment of the present invention when a part of a pixel read period is included in a vertical blanking period.

FIG. 6 is an illustrative diagram for explaining the read timing of the image sensor and the illumination timing of the illumination unit of the endoscope system according to the embodiment of the present invention when a part of the pixel read period is included in the vertical blanking period. As illustrated in FIG. 6, read periods R1a and R2a are periods required to read pixels to be image-processed and a vertical blanking period V11a may be a period other than periods to read pixels to be image-processed. The setting of the illumination period in this case may be the same as that of the vertical blanking period V11a or may be the same as that of the vertical blanking period V11 that is originally set. When the illumination period is set to be the vertical blanking period V11, the exposure period is longer than the illumination period.

In the embodiments, the light control unit 404 sets the illumination period according to the detection result of the brightness detection unit 403. However, even when the illumination period is changed by gain adjustment performed by a user, it is possible to change the vertical blanking period according to the changed illumination period. Further, when a liquid such as water is discharged from a water supply means provided in the endoscope 2 or when image distortion or color shift may occur due to the amount of liquid in an observed region, control may be performed so that the illumination period and the vertical blanking period are reduced. In this case, for example, control is performed according to pressing a water supply switch.

In the embodiments, the light control unit 404 sets the illumination period according to the detection result of the brightness detection unit 403. However, the illumination period may be set by acquiring the detection result of the brightness detection unit 403 for each frame, may be set by acquiring the detection result for each group of frames, or may be set by acquiring the detection result when the illumination is performed by using an illuminating light of a set wavelength band (for example, green light).

In the embodiments, the light control unit 404 sets the illumination period of the illumination unit 31 according to the detection result of the brightness detection unit 403. However, in the case of a configuration that does not include the illumination unit 31, the light control unit 404 may set, for example, an opening period of an electronic shutter of the image sensor 244 according to the detection result of the brightness detection unit 403. In the case of the device configuration according to the embodiments described above, the imaging device is configured by using the image sensor 244, the light control unit 404, and the drive information generation unit 408a. In the case of the device configuration according to the modified example described above, the imaging device is configured by using the image sensor 244, the drive information generation unit 224, and the light control unit 404. The imaging device may be configured by using the image sensor 244 and the drive information generation unit 224 and the drive information generation unit 224 may acquire an electrical signal from the AFE unit 244b or the P/S converter 244c and generate the drive information including the exposure period and the illumination period based on the electrical signal (brightness of an image).

In the embodiments, the control unit 408 of the processing device 4 controls the drive of the light source device 3 based on the acquired drive information. However, the light source device 3 may include a control unit and the control unit may acquire the drive information and drive based on the drive information.

In the embodiments, the red LED light source 311, the green LED light source 312, and the blue LED light source 313 are used as the light source unit 31a and the white LED light source is used as the light source unit 31c. However, a laser diode may be used as the light source. In the embodiments, the illumination unit 31 and the illumination unit 310 emit light of a wavelength band of any one of red, green, and blue. The illumination unit 31 and the illumination unit 310 may emit light of a wavelength band different from those described above.

According to some embodiments, it is possible to suppress the decrease of the frame rate without changing the clock rate of the reading.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
a light source unit configured to generate illuminating light to be emitted from a distal end of an insertion portion to be inserted into a subject;
an illumination controller configured to receive a light control signal and to control emission of the illuminating light from the distal end of the insertion portion according to the light control signal;
a light receiving unit in which a plurality of pixels is provided in a matrix form, each of the plurality of pixels being configured to perform photoelectric conversion on light from the subject irradiated with the illuminating light to generate an electrical signal;
a reading unit configured to sequentially read, for each line, the electrical signal generated by each of the pixels;
a light control unit configured to generate a first light control signal or a second light control signal, the first light control signal being input to the illumination controller to emit the illuminating light from the distal end of the insertion portion as a first pulsed light in a predetermined illumination period, the second light control signal being input to the illumination controller to emit the illuminating light from the distal end of the insertion portion as a second pulsed light in an illumination period shorter than the predetermined illumination period; and
an imaging controller configured to:
perform imaging control that alternately repeats read processing for causing the reading unit to sequentially read, for each line, the electrical signal from the light receiving unit, and exposure processing for exposing the light receiving unit;
perform imaging control such that, when the first light control signal is generated by the light control unit, the first pulsed light is emitted during a blanking period in which the plurality of pixels is exposed simultaneously after completion of reading of a last line of the light receiving unit by the reading unit until start of reading of a first line of the light receiving unit for a next frame; and
perform imaging control such that, when the second light control signal is generated by the light control unit, the blanking period is shortened compared to a case where the first light control signal is generated, without changing, from the case where the first light control signal is generated, a read period required for causing the reading unit to read from a first line for a predetermined frame to a last line for the predetermined frame in the light receiving unit, and the second pulsed light is emitted during the blanking period.

2. The endoscope system according to claim 1, further comprising a brightness detection unit configured to detect a brightness level from the electrical signal generated by the light receiving unit, wherein
the light control unit is configured to set an illumination period of the illuminating light according to the brightness level detected by the brightness detection unit, and
the imaging controller is configured to perform imaging control to set the blanking period according to the illumination period of the illuminating light set by the light control unit.

3. The endoscope system according to claim 1, wherein
the light source unit is configured to emit a plurality of illuminating rays of light having different wavelength bands in a switchable manner, and
the illumination controller is configured to switch between the plurality of illuminating rays of light having different wavelength bands for emission each time the exposure processing is performed.

4. The endoscope system according to claim 1, wherein the light source unit is configured to emit the illuminating light by pulse driving.

5. The endoscope system according to claim 4, wherein
the light control unit is configured to set an illumination period of the illuminating light emitted by the light source unit based on brightness of an image generated according to the electrical signal, and
the imaging controller is configured to perform imaging control such that the blanking period is equal to the illumination period set by the light control unit or is longer than the illumination period.

* * * * *